US012746009B2

(12) United States Patent
Huang et al.

(10) Patent No.: US 12,746,009 B2
(45) Date of Patent: *Sep. 29, 2026

(54) TISSUE CLAMPING SYSTEM

(71) Applicant: Shenzhen Lifevalve Medical Scientific Co. Ltd., Shenzhen (CN)

(72) Inventors: Guangnian Huang, Shenzhen (CN); Gang Wang, Shenzhen (CN)

(73) Assignee: Shenzhen Lifevalve Medical Scientific Co. Ltd., Shenzhen (CN)

( * ) Notice: Subject to any disclaimer, the term of this patent is extended or adjusted under 35 U.S.C. 154(b) by 281 days.

This patent is subject to a terminal disclaimer.

(21) Appl. No.: 18/682,063

(22) PCT Filed: Jul. 25, 2022

(86) PCT No.: PCT/CN2022/107620

§ 371 (c)(1),
(2) Date: Feb. 7, 2024

(87) PCT Pub. No.: WO2023/020204

PCT Pub. Date: Feb. 23, 2023

(65) Prior Publication Data

US 2025/0120723 A1 Apr. 17, 2025

(30) Foreign Application Priority Data

Aug. 19, 2021 (CN) ......................... 202110957089.0

(51) Int. Cl.
*A61F 2/24* (2006.01)
*A61B 17/122* (2006.01)
*A61B 17/128* (2006.01)

(52) U.S. Cl.
CPC ...... *A61B 17/1227* (2013.01); *A61B 17/1285* (2013.01)

(58) Field of Classification Search
CPC .... A61F 2/246; A61F 2/2466; A61B 17/1285; A61B 17/122; A61B 17/1227
See application file for complete search history.

(56) References Cited

U.S. PATENT DOCUMENTS

2023/0397990 A1* 12/2023 Wang ...................... A61F 2/246

FOREIGN PATENT DOCUMENTS

CN 111265340 A 6/2020
CN 113230001 A 8/2021

OTHER PUBLICATIONS

International Search Report dated Oct. 10, 2022 for corresponding PCT Application No. PCT/CN2022/107620.
First Office action in corresponding China Appl. No. 202110957089.0.

* cited by examiner

*Primary Examiner* — Jon Eric C Morales
(74) *Attorney, Agent, or Firm* — Raymond Sun

(57) ABSTRACT

A tissue clamping system (1) includes a tissue clamping device (100) and a driving component (200). The tissue clamping device (100) includes a clamping part (10), a first supporting part (20), a second supporting part (30), and a restricting part (40). The clamping part (10) includes at least two supporting arms (110) and at least two clamping arms (120) in one-to-one correspondence with the at least two supporting arms (110). The driving component (200) passes through the restricting part (40) and is detachably connected to the second supporting part (30), and the driving component (200) is configured to drive the at least two supporting arms (110) to expand or close radially with respect to the restricting part (40), so that the at least two clamping arms (120) expand or close radially with respect to the restricting part (40).

10 Claims, 10 Drawing Sheets

TISSUE CLAMPING SYSTEM

TECHNICAL FIELD

The present invention relates to the field of medical devices, and particularly to a tissue clamping system.

BACKGROUND ART

This section merely provides background information related to the present disclosure and is not necessarily prior art.

Mitral valve disease is a common disease in the elderly population. At present, there are already commercially available products for transcatheter mitral valve repair.

The principle of existing transcatheter mitral valve repair products is to use a clamping device to clamp the anterior leaflet and posterior leaflet of the mitral valve to reduce the valve opening area, so as to achieve the purpose of treating regurgitation. Among the existing products, some are mechanically locked clamping devices that require unlocking during the interventional operation to perform clamping, therefore making the operation complex. Moreover, due to the mechanical locking mechanism, the clamping stress is uncontrollable, resulting in significant damage to the leaflets. In order to avoid this problem, some use the elastic clamping mode, so that the leaflets are clamped between elastic clamping arms to alleviate the stress of the leaflets clamping and to reduce damage to the leaflets. It is necessary to use a certain mechanism to spread the elastic clamping arms before the leaflets are captured. The elastic clamping arm has a certain flexibility and poor stability, and may be offset during opening, thereby affecting the final valve clamping effect.

In order to solve the above-mentioned problems, it would be obvious to those of skill in the art to improve and optimize the elastic clamping arm. However, further optimization of the clamping effect is necessary.

SUMMARY OF THE INVENTION

Based on this, it is necessary to provide a tissue clamping system with good clamping effect.

A tissue clamping system includes a tissue clamping device and a driving component. The tissue clamping device includes a clamping part, a first supporting part, a second supporting part, and a restricting part. The clamping part includes at least two supporting arms and at least two clamping arms in one-to-one correspondence with the at least two supporting arms. The at least two supporting arms are provided on the first supporting part, and the at least two clamping arms are provided on the second supporting part. The second supporting part includes a guiding element. The restricting part passes through the first supporting part and is fixedly connected to the first supporting part. The driving component passes through the restricting part and is detachably connected to the second supporting part, and the driving component is configured to drive the at least two supporting arms to expand or close radially with respect to the restricting part, so that the at least two clamping arms expand or close radially with respect to the restricting part. In a closed state, a distal end of the restricting part is housed in the guiding element such that the distal end of the restricting part is housed in the guiding element at the first moment when the supporting arm is expanded.

In one embodiment, the distal end of the restricting part is housed in the guiding element when an included angle between the two supporting arms is 60° to 150°.

In one embodiment, the distal end of the restricting part is housed in the guiding element when an included angle between the two supporting arms is 120°.

In one embodiment, the tissue clamping device further includes a sealing part, the sealing part surrounding the restricting part.

In one embodiment, one end of the supporting arm is rotatably connected to the first supporting part, one end of the clamping arm is fixedly connected to the second supporting part, and the other end of the supporting arm is rotatably connected to the other end of the clamping arm.

In one embodiment, the supporting arm includes a curved section and a straight section, wherein one end of the curved section is fixedly connected to the straight section, and the other end is rotatably connected to the clamping arm. Alternatively, one end of the curved section is fixedly connected to the straight section, and one end of the straight section away from the curved section is rotatably connected to the clamping arm.

In one embodiment, in a closed position, the curved section is curved and a degree of curvature of the curved section increases as the clamping arm and the supporting arm move from the closed position to an open position.

In one embodiment, the clamping arm includes a connecting section and two supporting sections, two ends of the connecting section are separately connected to the two supporting sections, and an end where the connecting section is located is a free end of the clamping arm. Each of the supporting sections includes a curved segment and an extending segment, one end of the curved segment is connected to the extending segment, and the other end is connected to the connecting section, and an end of the curved segment away from the extending segment is not in the same plane as the extending segment, so that the connecting section is away from an axial central axis of the tissue clamping device.

In one embodiment, the extending segment includes a curved rod and a straight rod connected to the curved rod, an end of the curved rod away from the straight rod being connected to the curved segment.

In one embodiment, there are two clamping arms, and in the closed state, a connection region of the curved rod and the curved section of one clamping arm abuts against a connection region of the curved rod and the curved segment of the other clamping arm.

The tissue clamping system is provided with a restricting part and a second supporting part including a guiding element. The driving component passes through the restricting part, and in the closed state, the distal end of the restricting part is housed in the guiding element, and the restricting part and the guiding element encase the driving component, which may form a better restricting and reinforcing effect on the driving component. It is beneficial to the force stability of the supporting arm and the clamping arm at the first moment when the supporting arm is expanded, and thus no offset occurs during the subsequent further opening process and subsequent closing process, and the clamping effect is better.

DETAILED DESCRIPTION OF THE INVENTION

In order to make the above objects, features, and advantages of the present invention clearer and understandable, specific embodiments of the present invention will be described below in detail with reference to the accompanying drawings. In the following description, numerous specific details are set forth in order to provide a thorough understanding of the present invention. While the present invention may be implemented in many other ways other than those described herein, those skilled in the art may make similar modifications without departing from the spirit of the present invention, and thus the present invention is not limited to the specific embodiments disclosed below.

Unless defined otherwise, all technical and scientific terms used herein have the same meaning as commonly understood by one of ordinary skill in the art to which the present invention belongs. The terms are used herein in the description of the present invention for the purpose of describing specific embodiments only and are not intended to limit the present invention.

In the field of interventional medical devices, "distal end" is defined as an end away from an operator during the procedure and "proximal end" is defined as an end near the operator during the procedure. "Axial" refers to a direction parallel to the line between the center of the distal end and the center of the proximal end of the medical device.

Figure 1:
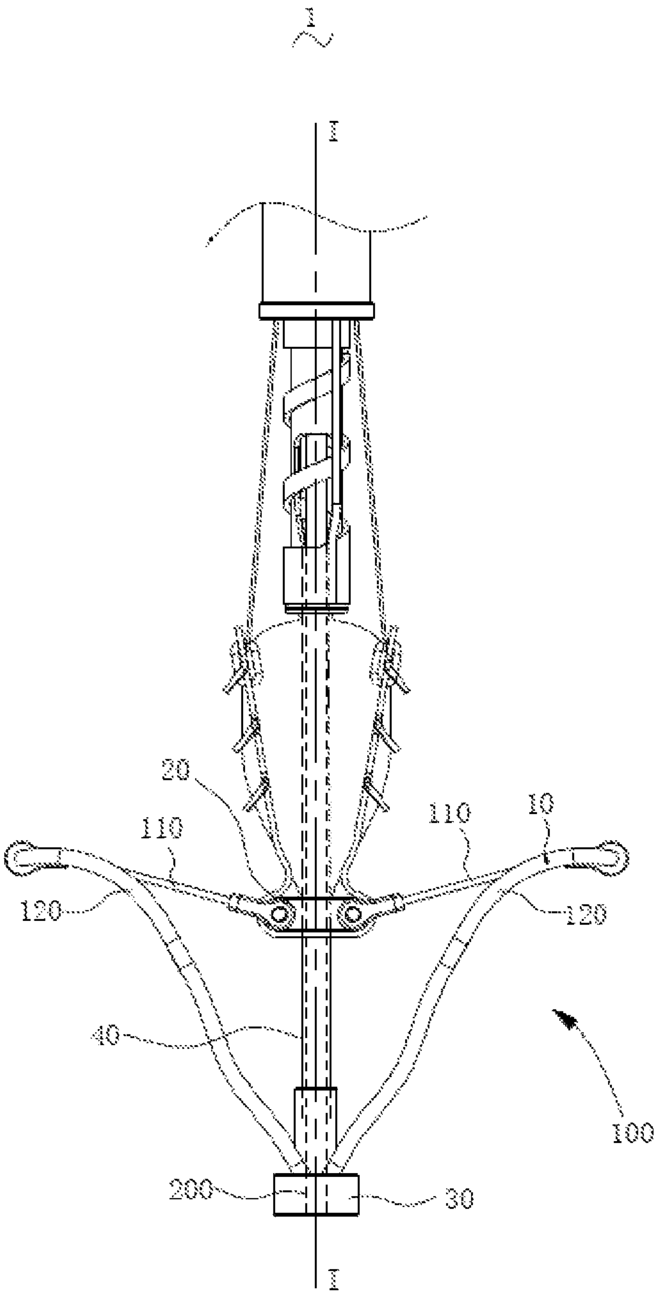
FIG. 1 is a schematic diagram of the open state of a tissue clamping system according to an embodiment.
Figure 2:
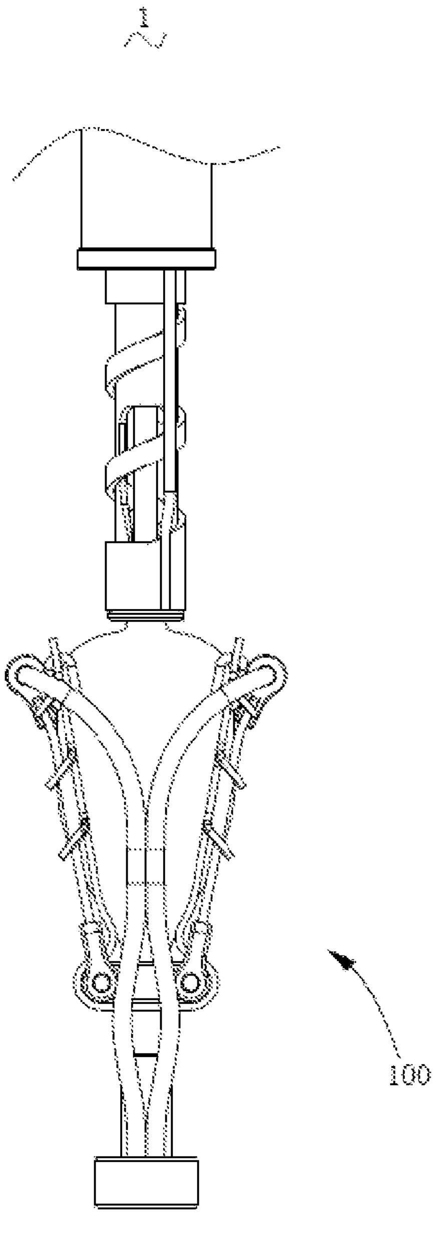
FIG. 2 is a schematic diagram of the closed state of a tissue clamping system according to an embodiment.

Referring to FIG. 1, a tissue clamping system 1 according to one embodiment includes a tissue clamping device 100 and a driving component 200 (in the state shown in FIG. 1, the driving component 200 is not visible, but in order to clearly illustrate the mating relationship between the driving component 200 and other elements, the driving component 200 is indicated by dashed lines). The tissue clamping device 100 is configured to clamp tissues. The tissues include, but are not limited to, the leaflets of the mitral valve, the leaflets of the tricuspid valve, etc. The driving component 200 is configured to drive the tissue clamping device 100 such that the tissue clamping device 100 may be moved between an open position and a closed position, i.e. changed between an open state and a closed state, to clamp the tissue after catching the tissue. Here, the state shown in FIG. 1 is an open state, and the state shown in FIG. 2 is a closed state.

The tissue clamping device 100 includes a clamping part 10, a first supporting part 20, a second supporting part 30, and a restricting part 40.

The clamping part 10 includes at least two supporting arms 110 and at least two clamping arms 120 in one-to-one correspondence with the at least two supporting arms 110. In the embodiment shown in FIG. 1, the number of supporting arms 110 is two and the number of clamping arms 120 is two. The two supporting arms 110 are provided on the first supporting part 20. Specifically, the two supporting arms 110 are arranged symmetrically with an axial central axis of the first supporting part 20 as a symmetrical axis. The two clamping arms 120 are provided on the second supporting part 30. Specifically, the two clamping arms 120 are arranged symmetrically with an axial central axis of the second supporting part 30 as a symmetrical axis. The axial central axis of the first supporting part 20 and the axial central axis of the second supporting part 30 are collinear or coincide with an axial central axis I-I of the tissue clamping device 100.

An axial central axis of the driving component 200 is collinear or coincident with the axial central axis I-I of the tissue clamping device 100. Under the drive of the driving component 200, the two supporting arms 110 may be radially expanded or closed with respect to the axial central axis I-I of the tissue clamping device 100, and the two clamping arms 120 may be radially expanded or closed with respect to the axial central axis I-I of the tissue clamping device 100.

In one embodiment, one end of the supporting arm 110 is rotatably connected to the first supporting part 20 such that the supporting arm 110 may be radially expanded or closed with respect to the axial central axis I-I of the tissue clamping device 100 under the drive of the driving component 200.

In one embodiment, the material of the supporting arm 110 is an elastic metal, such as nickel titanium alloy and elastic stainless steel.

In one embodiment, the supporting arm 110 is a sheet structure, a rod structure, or a coil structure, etc.

One end of the clamping arm 120 is fixedly connected to the second supporting part 30, and one end of the supporting arm 110 away from the first supporting part 20 is rotatably connected to the other end of the clamping arm 120, so that when the driving component 200 moves in an axial direction, the supporting arm 110 and the clamping arm 120 may be radially expanded or closed at the same time. That is, the supporting arm 110 and the clamping arm 120 are movable between an open position (as shown in FIG. 1) and a closed position (as shown in FIG. 2).

One end of the supporting arm 110 away from the first supporting part 20 is rotatably connected to the other end of the clamping arm 120, for example, the rotatable connection may be achieved by a rotating shaft, a pin, a movable hinge, or the like.

Figure 3:
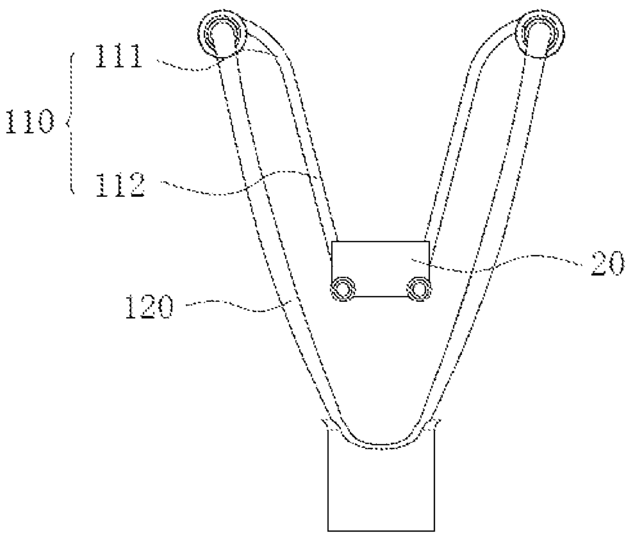
FIG. 3 is a schematic diagram of a connection state of a supporting arm and a clamping arm according to an embodiment.
Figure 4:
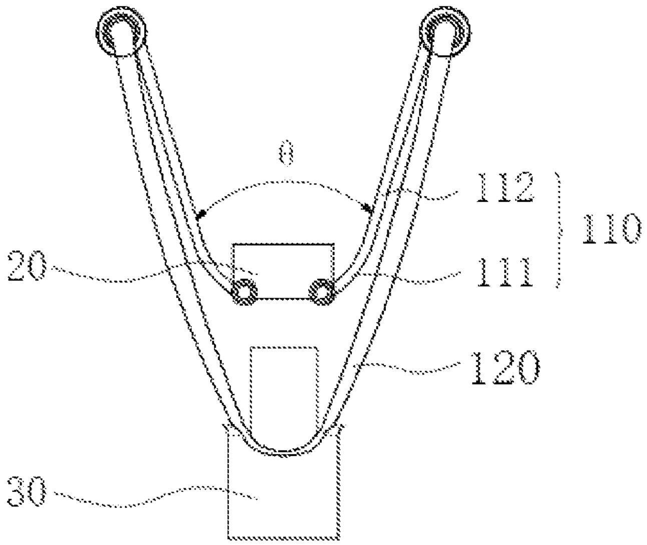
FIG. 4 is a schematic diagram of a connection state of a supporting arm and a clamping arm according to another embodiment.

Referring to FIG. 3, the supporting arm 110 includes a curved section 111 and a straight section 112. One end of the curved section 111 is fixedly connected to the straight section 112, and the other end is rotatably connected to the clamping arm 120. One end of the straight section 112 away from the curved section 111 is rotatably connected to the first supporting part 20. Referring to FIG. 4, in another embodiment, one end of the curved section 111 is fixedly connected to the straight section 112 and the other end is rotatably connected to the first supporting part 20, and one end of the straight section 112 away from the curved section 111 is rotatably connected to the clamping arm 120.

Figure 5:
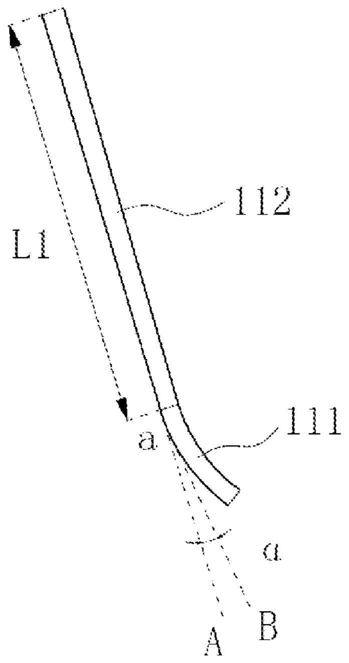
FIG. 5 is a schematic structural diagram of a supporting arm according to an embodiment.

Referring to FIG. 5, in one embodiment, the straight section 112 has a length L1 and the curved section 111 has an arc length L2 (not shown), where L2/L1=⅕-⅓. The lengths of the straight section 112 and the curved section 111 are set in this way such that, on the one hand, the curved section 111 is prevented from being excessively long so as to ensure that a sufficient spreading force is transmitted to the clamping arm 120, i.e., ensuring that the supporting arm 110 may provide a certain spreading force such that the clamping arm 120 may be spread during the opening process; on the other hand, the curved section 111 is prevented from being excessively short such that the curved section 111 may be further deformed (further curved) during the opening process to alleviate the excessive stress.

With continued reference to FIG. 5, in one embodiment, the curved section 111 has an angle α ranging from 10° to 45° which ensures that the supporting arm 110 may transmit the spreading force to the clamping arm 120 under a certain force, and that the curved section 111 may deform to some extent to alleviate the excessive stress. The angle α refers to an included angle between an extension line A of the straight section 112 and a tangent line B of the curved section 111, and the tangent line B intersects the extension line A at the intersection point a of the extension line A with the curved section 111. The intersection point a is a tangent point of the tangent line B.

When the length of the supporting arm 110 is determined, the greater the angle α of the curved section 111, the smaller the capture length of the supporting arm 110, and the more difficult it is to capture the tissue. When the angle α of the curved section 111 is too small, it is difficult to realize the function of easily opening the clamping arm 120. Therefore, in one embodiment, the straight section 112 has a length L1 and the curved section 111 has an arc length L2, where L2/L1=⅕-⅓, and the curved section 111 has an angle α ranging from 10° to 45°, so as to easily open the clamping arm 120 and capture the tissue, facilitating the operation, making the surgery go smoothly, and reducing the surgery time.

In one embodiment, the supporting arm 110 may be a unitary structure made of metal wire or sheet materials which, after the heat-setting, produce corresponding curved shapes to form the curved section 111 and the straight section 112.

In one embodiment, as the supporting arm 110 and the clamping arm 120 move from the closed position to the open position, a degree of curvature of the curved section 111 increases. That is, the curved section 111 may guide the supporting arm 110 to deform in the curved direction when the force exceeds a certain limit, so as to play a buffering role. When the supporting arm 110 deforms to a certain extent, the clamping arm 120 opens more easily.

Figure 6:
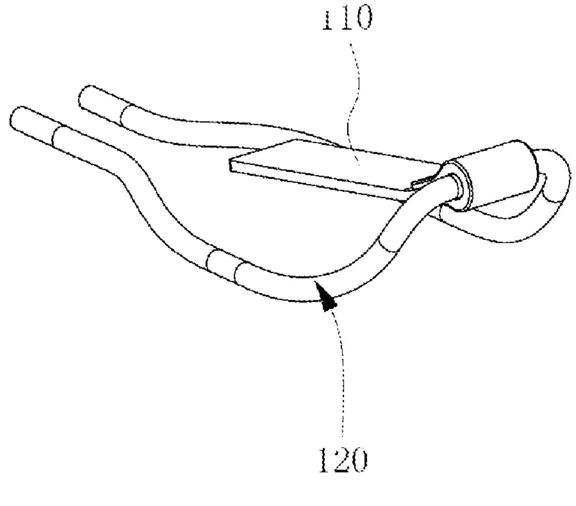
FIG. 6 is a schematic structural diagram of a clamping arm according to an embodiment.

In one embodiment, as shown in FIG. 6, the clamping arm 120 is generally a wire loop structure having an opening. For example, the clamping arm 120 may be a wire loop having an opening that is formed by a nickel-titanium wire. One end of the supporting arm 110 connected to the clamping arm 120 is curved or rolled to encase the clamping arm 120, so that the supporting arm 110 is rotatably connected to the clamping arm 120. This connection is achieved by the structures of the supporting arm 110 and the clamping arm 120 themselves cooperating with each other, so that the supporting arm 110 and the clamping arm 120 may be pivoted relative to each other without using connectors such as a rotating shaft and a pin. This pivotal connection reduces the use of rotating shafts, pins, or the like, and may provide for flexible rotation.

It will be appreciated that an end of the supporting arm 110 that is curved or rolled to encase the clamping arm 120 may be an end of the curved section 111 away from the straight section 112 or an end of the straight section 112 away from the curved section 111.

Figure 7:
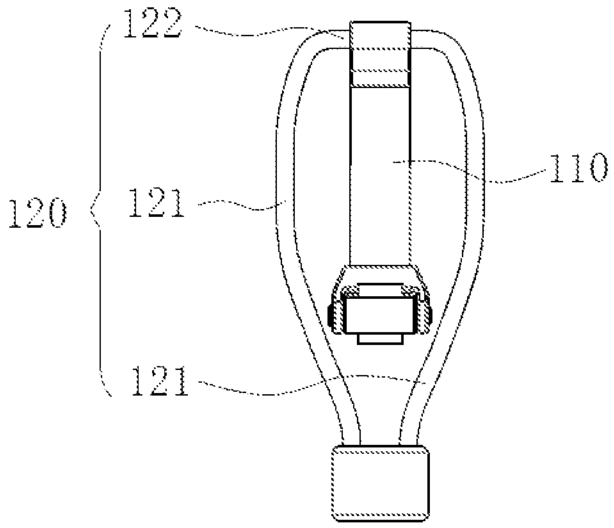
FIG. 7 is a schematic structural diagram of another angle of a clamping arm according to an embodiment.

Referring to FIG. 7, in one embodiment, the clamping arm 120 includes two supporting sections 121 and a connecting section 122 which are metal rods. Two ends of the connecting section 122 are separately connected to the two supporting sections 121, and the ends of the two supporting sections 121 away from the connecting section 122 are not connected to form a wire loop structure having an opening. An end where the connecting section 122 is located is a free end of the clamping arm 120. The supporting arm 110 is rotatably connected to the connecting section 122.

Figure 8:
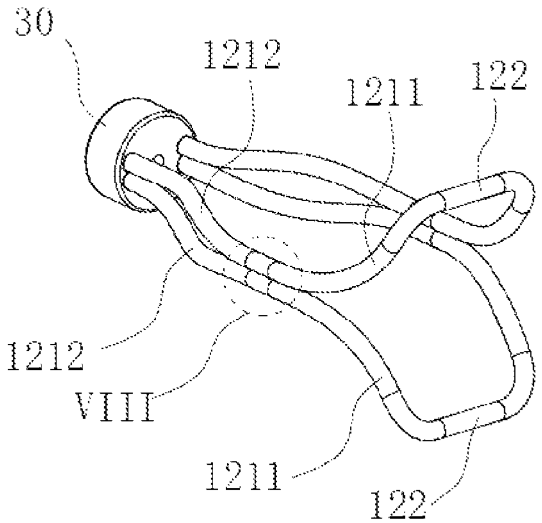
FIG. 8 is a schematic diagram of the positional relationship of two clamping arms in the closed state according to an embodiment.

Referring collectively to FIG. 8, in one embodiment, each of the supporting sections 121 includes a curved segment 1211 and an extending segment 1212 connected to the curved segment 1211. An end of the curved segment 1211 away from the extending segment 1212 is curved in a first direction such that an end of the curved segment 1211 away from the extending segment 1212 is not in the same plane as the extending segment 1212. Also, because the end of the curved segment 1211 away from the extending segment 1212 is curved in the first direction, the connecting section 122 of the clamping arm 120 is away from the axial central axis I-I of the tissue clamping device 100.

As shown in FIG. 8, in a natural state, the curved segment 1211 is curved in the first direction, and the curvature of the curved segment 1211 makes one end of the curved segment 1211 away from the extending segment 1212 to not be in the same plane as the extending segment 1212, so that the free ends of the two clamping arms 120 are away from the axial central axis I-I, i.e., the two connecting sections 122 of the two clamping arms 120 are away from the axial central axis I-I and away from each other, so that the clamping arms 120 are easily opened. The first direction, for example, as shown in FIG. 8, may be a direction away from the connecting section 122 of the other clamping arm 120, and the end of the curved segment 1211 away from the extending segment 1212 is not in the same plane as the extending segment 1212.

In one embodiment, the extending segment 1212 is in the shape of a straight rod, and the region where the extending segment 1212 connects to the curved segment 1211 is in the same plane as the extending segment 1212.

Figure 9:
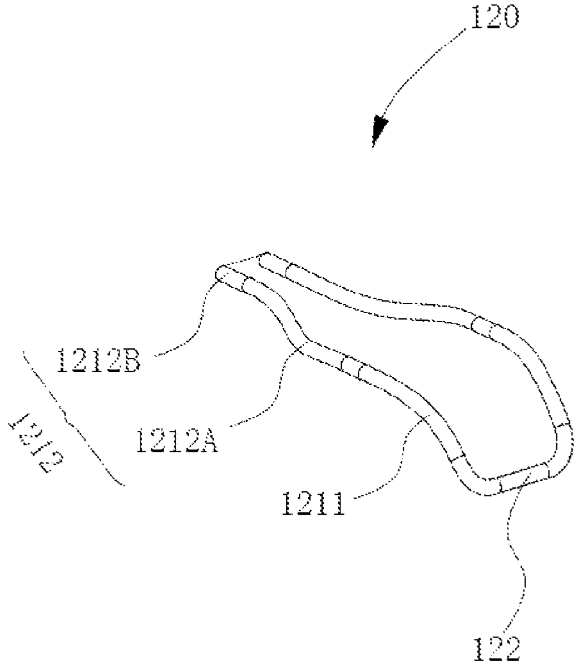
FIG. 9 is a schematic structural diagram of a clamping arm according to an embodiment.
Figure 10:
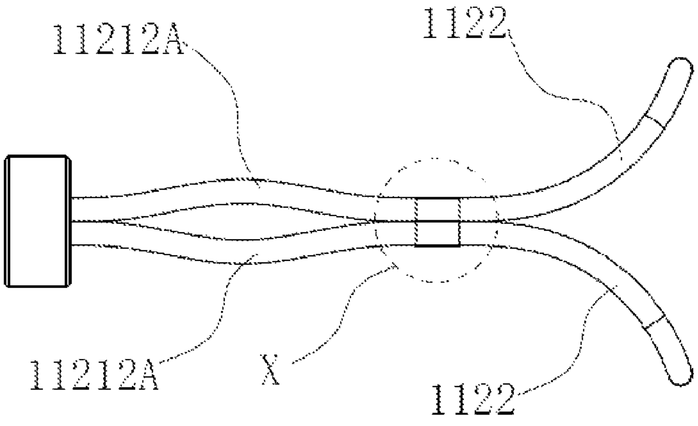
FIG. 10 is a schematic diagram of the positional relationship of the two clamping arms of FIG. 8 shown at another angle.

Referring to FIG. 9, in one embodiment, the extending segment 1212 includes a curved rod 1212A and a straight rod 1212B connected to the curved rod 1212A, and an end of the curved rod 1212A away from the straight rod 1212B is connected to the curved segment 1211. Referring to FIGS. 8 and 10 together, in one embodiment, in a natural state (also a closed state), the curved rod 1212A is curved in a second direction such that a connection region between the curved rod 1212A and the curved segment 1211 of one clamping arm 120 abuts reliably against a connection region between the curved rod 1212A and the curved segment 1211 of the other clamping arm 120 (the circle indicated by X in FIG. 10) to form an abutting region. At the abutting region, since the clamping arm 120 has elasticity, the two clamping arms 120 provide opposing abutting force to each other, so that the two clamping arms 120 abut reliably against each other, which is beneficial to improving the reliability of clamping, so as to prevent the tissue clamping device 100 from falling off due to the contraction and relaxation motion of the heart. The second direction, for example, as shown in FIG. 9, may be a direction outside the wire loop, i.e. with the circle center of the curved rod 1212A itself being located inside the wire loop.

In one embodiment, the connection region of the curved rod 1212A and the curved segment 1211 of each of the clamping arms 120 is in the shape of a straight rod, so that the region of the two clamping arms 120 abutting against each other has a larger area to abut against more reliably.

Figure 11:
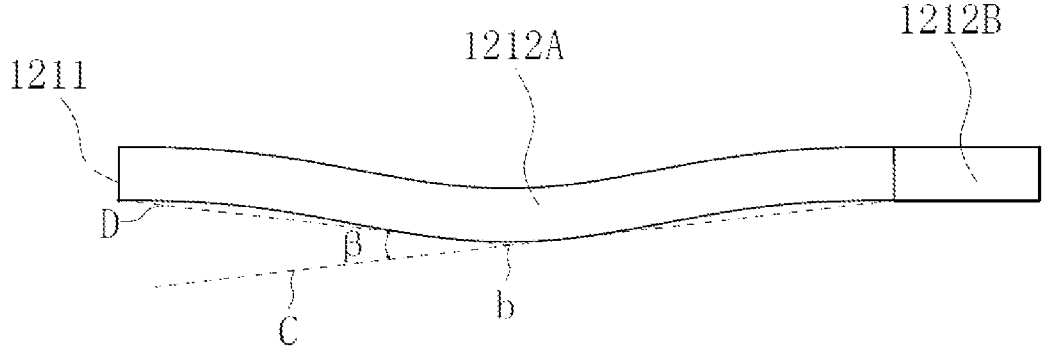
FIG. 11 is a schematic diagram of a partial structure of a clamping arm according to an embodiment.

Referring to FIG. 11, in one embodiment, the curved rod 1212A has an angle β between 5° and 15° to allow the connection regions of the extending segments 1212 and the curved segments 1211 of the two clamping arms 120 to abut reliably against each other. The angle β refers to an angle formed by the intersection of the tangent line C and the tangent line D of the curved rod 1212A, and the intersection point is b. The tangent line C intersects the junction of the curved rod 1212A and the straight rod 1212B and the tangent line D intersects the junction of the curved rod 1212A and the curved segment 1211.

Figure 12:
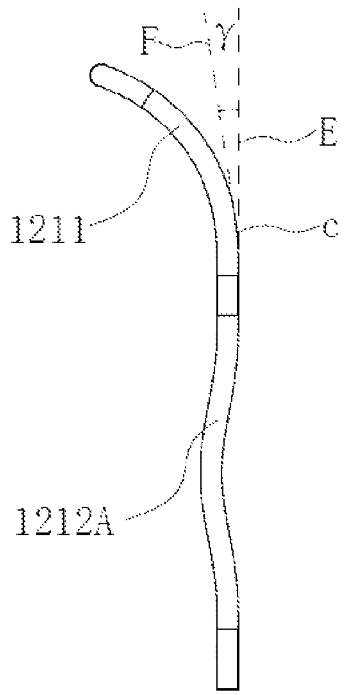
FIG. 12 is a schematic diagram of a partial structure of a clamping arm according to an embodiment.

Referring to FIG. 12, in one embodiment, the curved segment 1211 has an angle γ between 10° and 60° to facilitate opening of the clamping arm 120, and when the length of the curved segment 1211 is constant, the region of the curved segment 1211 that connects with the curved rod 1212A (i.e., the region of the curved segment 1211 that is coplanar with the curved rod 1212A) is long enough to maintain clamping. The angle γ refers to an included angle between the extension line E of the connection region of with the curved rod 1212A and the curved segment 1211 and the tangent line F of the curved segment 1211, and the tangent line F intersects with the extension line E at the intersection point c of the extension line E with the curved section 1112.

Figure 13:
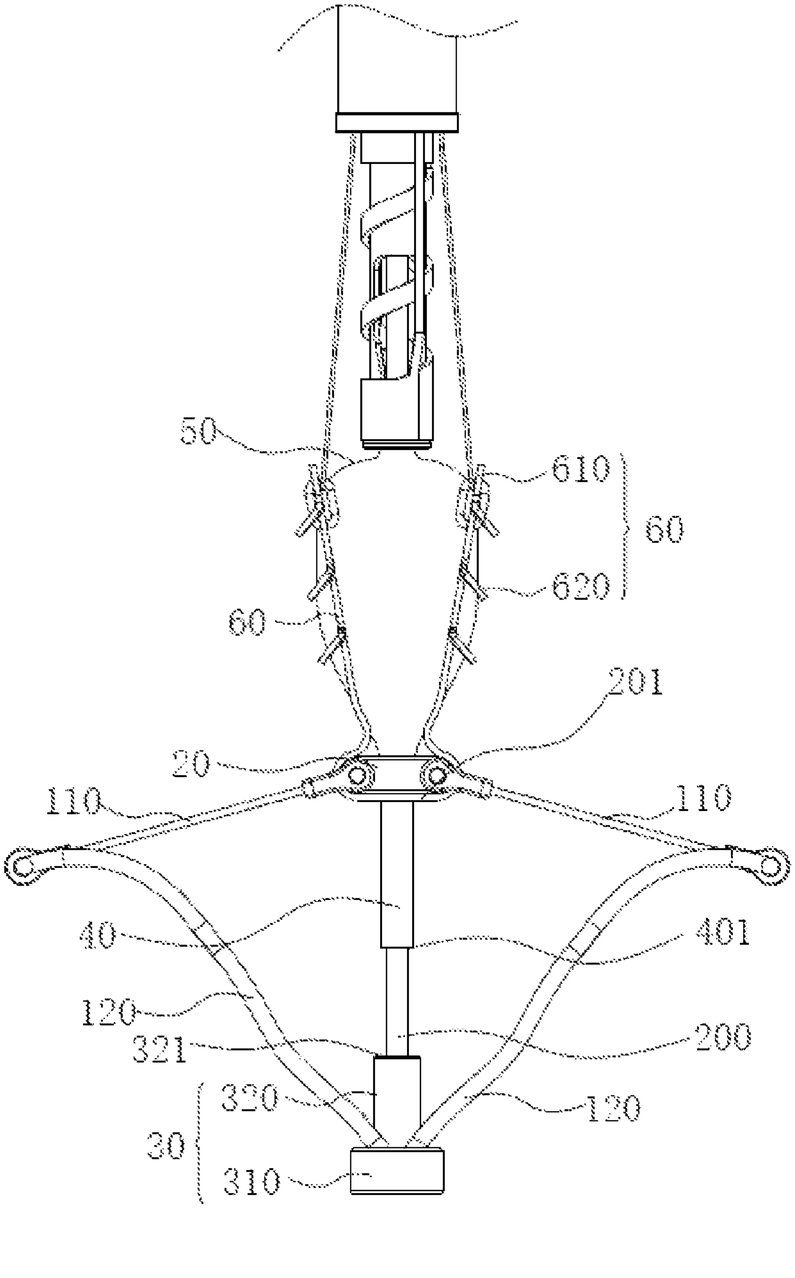
FIG. 13 is a schematic diagram of the open state of a tissue clamping system according to an embodiment.

As shown in FIG. 13, the first supporting part 20 and the second supporting part 30 are opposed in the axial direction and are coaxially and spaced apart.

In one embodiment, the first supporting part 20 is generally a columnar structure. An end of the supporting arm 110 away from the clamping arm 120 is rotatably connected to the first supporting part 20. For example, it is connected by means of a rotating shaft so that the supporting arm 110 is rotatable with respect to the first supporting part 20. A first through hole (not shown) is formed in the middle of the first supporting part 20.

With continued reference to FIG. 13, the second supporting part 30 includes a base 310 and a guiding element 320 disposed on the base 310. The base 310 is generally a cylindrical structure, and the guiding element 320 is a hollow columnar structure. The guiding element 320 extends axially from a side of the base 310 adjacent to the first supporting part 20 to a direction adjacent to the first supporting part 20. The base 310 and the guiding element 320 may be of unitary structure. Alternatively, the base 310 and the guiding element 320 may be fixedly connected in a manner known to those skilled in the art, including, but not limited to, welding, gluing, etc.

An end of the clamping arm 120 away from the supporting arm 110 is fixedly connected to the second supporting part 30. Specifically, the clamping arm 120 is connected to the base 310 of the second supporting part 30 through the supporting section 121. An end of the straight rod 1212B of the supporting section 121 away from the curved rod 1212A is fixedly connected to the base 310.

With continued reference to FIG. 13, the restricting part 40 is a hollow tubular member. The restricting part 40 passes through the first supporting part 20 from the first through hole of the first supporting part 20 and is fixedly connected to the first supporting part 20. The restricting part 40 extends from the first supporting part 20 such that a distal end face 401 of the restricting part 40 is spaced from a distal end face 201 of the first supporting part 20.

The restricting part 40 has a certain rigidity. In one embodiment, the restricting part 40 is a nickel titanium tube, a stainless steel tube or the like. The outer diameter of the restricting part 40 is smaller than the inner diameter of the guiding element 320.

In one embodiment, the tissue clamping device 100 further includes a sealing part 50. The sealing part 50 is adapted to surround the restricting part 40. Also, one end of the sealing part 50 is fixedly connected to the first supporting part 20, and the other end of the sealing part 50 is used to be connected to a transport system. A sealing part 50 is provided, and the sealing part 50 may seal and fill the gap between the two tissues, so as to further improve the sealing effect. In one embodiment, the sealing part 50 is made of an elastic material so that the sealing part 50 has a certain deformability, and after clamping, the sealing part 50 may play a certain buffering role, so that the two tissues that are clamped (e.g. two leaflets) are not drawn together in a stressed connection, thereby reducing the clamping stress.

The shape of the sealing part 50 is not limited, and any shape capable of performing a sealing and buffering function may be used. In one embodiment, the sealing part 50 is cylindrical. In another embodiment, the sealing part 50 is small at two axially opposite ends and large in the middle.

In one embodiment, the shape of the sealing part 50 matches the shape of the clamping arm 120 such that in the clamped state, the outer surface of the sealing part 50 completely fills the wire loop of the clamping arm 120, thereby improving the sealing effect.

In one embodiment, the sealing part 50 is provided with a cover film (not shown) that covers the surface of the sealing part 50 to further improve the sealing effect.

The driving component 200 is a rod structure, and the outer diameter of the driving component 200 is smaller than the inner diameter of the restricting part 40. The driving component 200 is detachably connected to the second supporting part 30.

In one embodiment, the driving component 200 is detachably connected to the second supporting part 30 by a thread. For example, the base 310 of the second supporting part 30 is provided with a threaded hole, and a distal end of the driving component 200 is provided with a thread cooperating with the threaded hole to achieve a detachable connection.

Further, the driving component 200 movably passes through the restricting part 40 and is axially slidable along the restricting part 40. The axial sliding of the driving component 200 enables the tissue clamping device 100 to move between the open position and the closed position. As the driving component 200 slides axially to the distal end, the supporting arm 110 expands radially to spread the clamping arm 120, so that the clamping arm 120 also expands radially. As the driving component 200 slides axially to a proximal end, the clamping arm 120 moves with the supporting arm 110 in a closing direction.

With continued reference to FIG. 13, in one embodiment, the tissue clamping device 100 further includes gripping parts 60. In one embodiment, there are two gripping parts 60, and the two gripping parts 60 surround both sides of the sealing part 50. One end of each of the gripping parts 60 is connected to the first supporting part 20, and the other end is a free end. The gripping part 60 is configured to grip the tissues to improve surgical efficiency and success rate.

In one embodiment, the gripping part 60 includes a body 610 and a plurality of anchors 620 spaced on the body 610. One end of the body 610 is connected to the first supporting part 20, and the other end is a free end. One end of the anchor 620 is connected at an acute angle to the body 610 and the other end is a free end that extends outward and towards the supporting arm 110.

Figure 14:
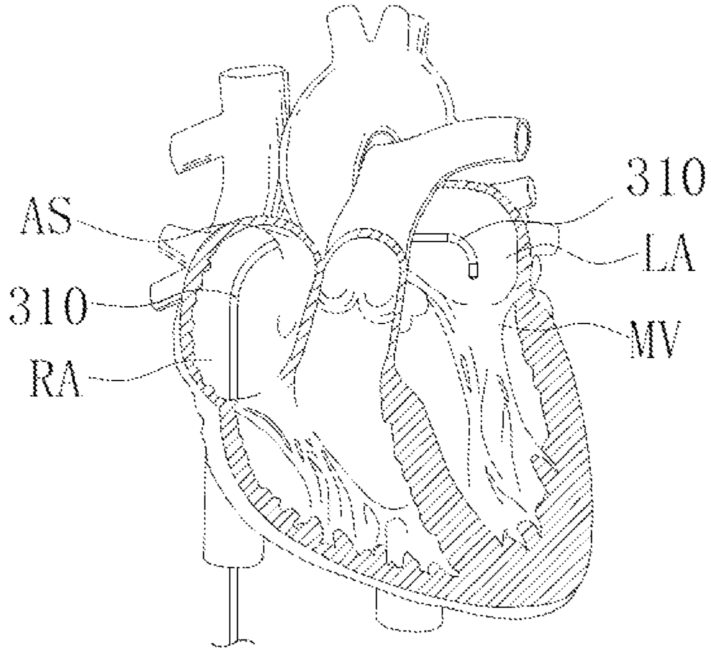
FIGS. 14-17 are schematic diagrams of an implantation process of a tissue closure device according to an embodiment.
Figure 15:
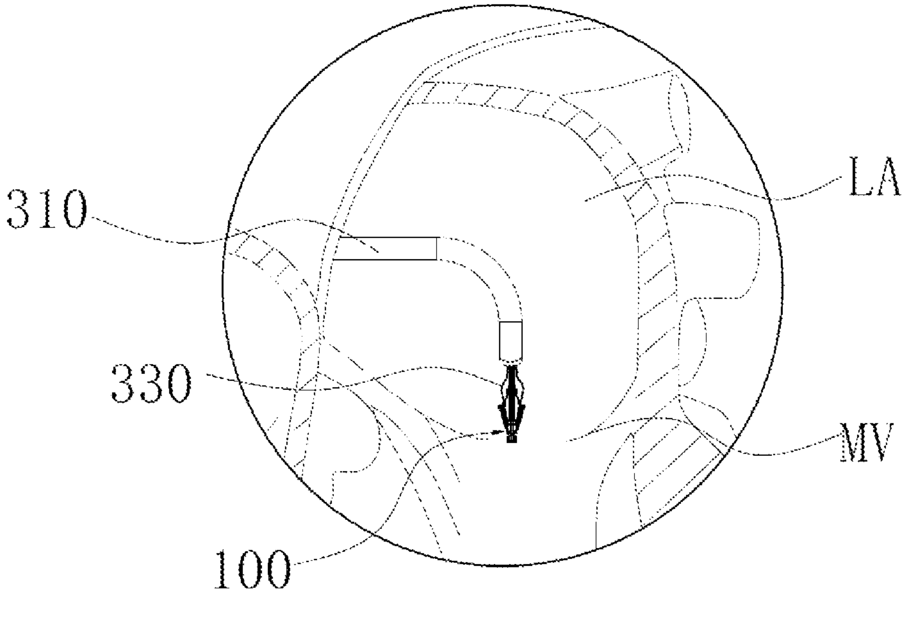
Figure 16:
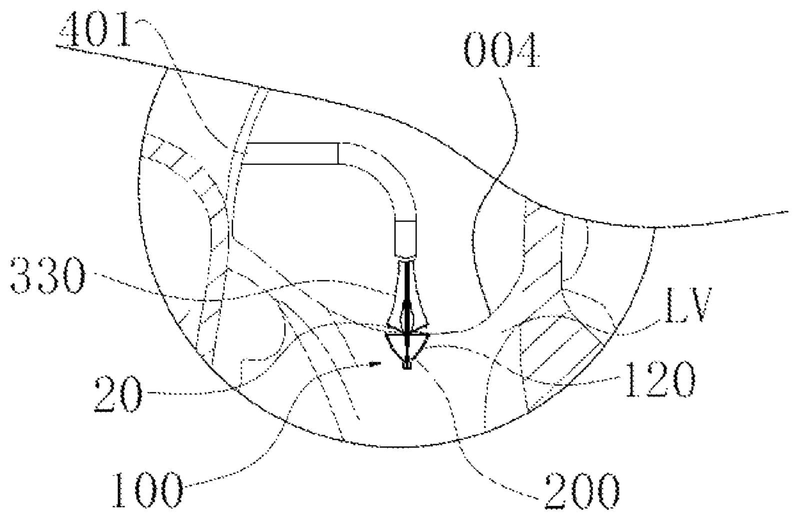
Figure 17:
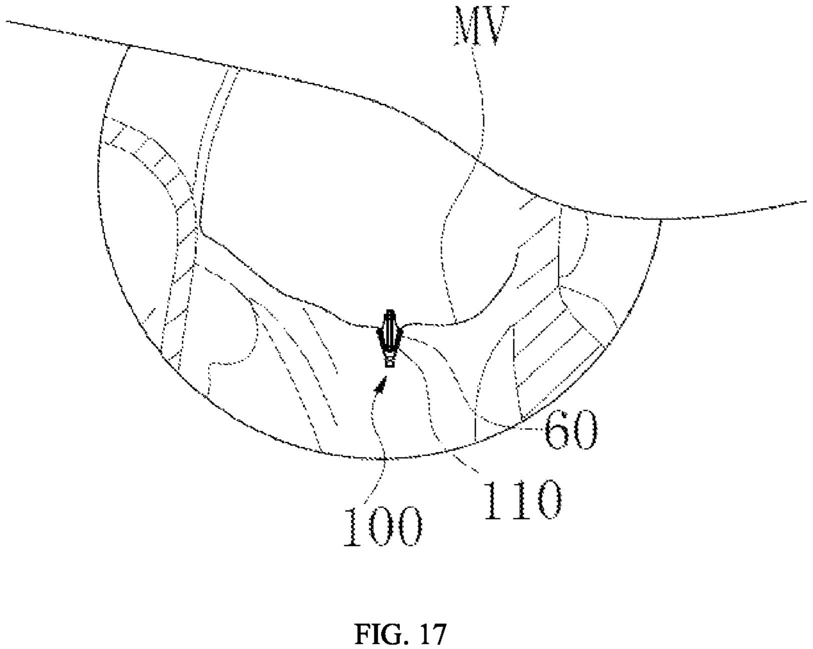

The transportation, release and closure process of the tissue clamping device 100 is described with the tissue to be closed being mitral valve leaflets as an example. In one embodiment, as shown in FIG. 14, a transporting sheath 310 passes through the femoral vein and the inferior vena cava to the right atrium RA, and then punctures the atrial septum AS, so that a distal end of the transporting sheath 310 reaches the left atrium LA. The tissue clamping device 100 is advanced out of the transporting sheath 310 by adjusting the distal end of the transporting sheath 310 such that it is centered over the mitral valve MV and then manipulating the control on the handle, as shown in FIG. 15. Further, referring to FIG. 16, the tissue clamping device 100 is advanced to the mitral valve MV position and the position is adjusted (if necessary) so that the clamping arm 120 of the tissue clamping device 100 is located on a side of the mitral valve leaflets close to the left ventricle LV. By manipulating the control on the handle, the driving component 200 is moved axially so that the supporting arm 110 and the clamping arm 120 are in an open state to capture the leaflets. The angle of the gripping part 60 is then controlled by the control wire 330 to capture the leaflets. After the gripping part 60 captures the leaflets, the driving component 200 is moved axially such that the supporting arm 110 and the clamping arm 120 move from the open position to the closed position to clamp the leaflets between the gripping part 60 and the supporting arm 110, as shown in FIG. 17, thereby achieving a reduction in the opening area of the mitral valve MV. After the clamping is completed, the control wire 330 is withdrawn, the driving component 200 is disconnected from the second supporting seat 30, the connector is disconnected from the tissue closure device 100, and the transporter is withdrawn, thereby completing the surgery.

In the closed state, a distal end of the restricting part 40 is housed in the guiding element 320 such that the distal end of the driving component 200 is covered by the restricting part 40 and the guiding element 320 while being restrained by the restricting part 40 and the guiding element 320. When the tissue clamping device 100 is to be opened, at the first moment of opening, the acting force generated on the clamping arm 120 is the maximum, the restricting part 40, the guiding element 320 and the driving component 200 form a rigid guiding element structure, and the positioning and guiding action of the rigid guiding element structure facilitates the stable transmission of the acting force and its uniform distribution to the two sides, so as to avoid the offset of the clamping arm 120, thereby enabling the two clamping arms 120 on the two sides to be synchronously and stably opened.

In addition, the distal end of the restricting part 40 is housed in the guiding element 320, and the distal end of the driving component 200 is covered by the restricting part 40 and the guiding element 320, which serves to enhance rigidity, maximize the force effectively transmitted by the driving, and facilitate the opening of the clamping arm 120.

Meanwhile, due to the rigidity-enhancing effect of the restricting part 40 and the guiding element 320, it is possible to use the driving component 200 with a small outer diameter, so that the overall flexibility of the tissue clamping system 1 is better for passing through a curved lumen.

In one embodiment, the distal end of the restricting part 40 is housed in the guiding element 320 when an included angle θ (as shown in FIG. 4) of the two supporting arms 110 is 60° to 150°. When the included angle θ of the two supporting arms 110 is 60° to 150°, the distal end of the restricting part 40 is maintained and housed in the guiding element 320, and the distal end of the driving component 200 is covered by the restricting part 40 and the guiding element 320, so that the force on the left and right sides of the axial central axis I-I of the tissue clamping device 100 is uniform, which is beneficial to ensure that no offset occurs during the subsequent opening process and subsequent closing process, thereby improving the clamping effect.

In one embodiment, when the included angle θ of the two supporting arms 110 is 120°, the distal end of the restricting part 40 is housed in the guiding element 320 to ensure that no offset occurs during the further opening process and the subsequent closing process, thereby improving the clamping effect.

In the state shown in FIG. 13, the included angle θ of the two supporting arms 110 is greater than 180°, which is the state ready for retraction, i.e. a transition point between the open state and the closed state. At this point, the distal end of the restricting part 40 has been disengaged from the guiding element 320, and the distal end face 401 of the restricting part 40 is spaced from a proximal end face 321 of the guiding element 320, exposing the driving component 200. Meanwhile, the distal end of the driving component 200 is still connected with the base 310.

It should be noted that the included angle θ of the two supporting arms 110 refers to an included angle enclosed by the two supporting arms 110 on the side away from the second supporting part 30.

The tissue clamping system 1 is provided with a restricting part 40 and a second supporting part 30 including a guiding element 320, wherein the driving component 200 passes through the restricting part 40, and in a closed state, a distal end of the restricting part 40 is housed in the guiding element 320, and the restricting part 40 and the guiding element 320 encase the driving component 200, which may form a better restricting and reinforcing effect on the driving component 200. It is beneficial to the force stability of the supporting arm 110 and the clamping arm 120 at the first moment when the supporting arm 110 is expanded or opened, and thus no offset occurs during the subsequent further opening process and subsequent closing process, and the clamping effect is better.

It should be noted that in one embodiment, the base 310 in the second supporting part 30 may be omitted. When the base 310 is omitted, the clamping arm 120 is directly connected to the guiding element 320, e.g. the straight rod 1212B of the clamping arm 120 is directly connected to the outer wall of the guiding element 320. Also, the distal end of the driving component 200 is provided with a connecting part threadedly connected with the inner wall of the guiding element 320, and the connecting part has an outer diameter larger than that of the remaining parts of the driving component 200, so that the distal end of the restricting part 40 may be housed in the guiding element 320 in a state where the driving component 200 remains connected with the guiding element 320.

Further, since the supporting arm 110 of the tissue closure device 100 includes the curved section 111 and the straight section 112, the component force of the supporting arm 110 applied to the clamping arm 120 in an opening direction is increased during the opening process, making the opening of the clamping arm 120 easier, thereby improving the safety of the manipulation system.

Furthermore, due to the special structural design of the clamping arm 120, the free ends of the two clamping arms 120 are away from the axial central axis I-I, so that the opening of the clamping arm 120 is easier, and the supporting arm 110 may spread the clamping arm 120 using a smaller force, so that the connecting section 122 of the clamping arm 120 is moved away from the axial central axis I-I, and thus the clamping arm 120 is in an open state.

Also, since one end of the curved segment 1212 of the clamping arm 120 near the extending segment 1211 is located in the same plane as the extending segment 1211, in the closed position, the two clamping arms 120 may reliably clamp the sealing part 50 to avoid falling off and therefore maintain sealing performance.

It should be noted that in other embodiments, the sealing part 50 may be omitted, and in the closed state, the two clamping arms 120 surrounded both sides of the restricting part 40 close to each other and abut against each other, so that a preferable clamping effect may be achieved. However, by providing the sealing part 50, the clamping effect and the sealing effect may be further improved.

Various technical features of the embodiments above may be arbitrarily combined. In order to make the description concise, not all the possible combinations of various technical features in the embodiments above are described. However, the combinations of these technical features shall be considered as falling within the scope of the description as long as there is no contradiction therein.

The embodiments described above represent only a few implementations of the present invention which are described in more detail, but are not to be construed as limiting the scope of the present invention. It should be noted that a person of ordinary skill in the art would be able to make several variations and improvements without departing from the concept of the present invention, which fall within the protection scope of the present invention. Therefore, the protection scope of the present invention shall be subject to the appended claims.

The invention claimed is:

1. A tissue clamping system, comprising a tissue clamping device and a driving component, wherein the tissue clamping device comprises a clamping part, a first supporting part, a second supporting part, and a restricting part; the clamping part comprises at least two supporting arms and at least two clamping arms in one-to-one correspondence with the at least two supporting arms, the at least two supporting arms are provided on the first supporting part, and the at least two clamping arms are provided on the second supporting part; the second supporting part comprises a guiding element, and the restricting part passes through the first supporting part and is fixedly connected to the first supporting part; the driving component passes through the restricting part and is detachably connected to the second supporting part, and the driving component is configured to drive the at least two supporting arms to expand or close radially with respect to the restricting part, so that the at least two clamping arms expand or close radially with respect to the restricting part; in a closed state, a distal end of the restricting part is housed in the guiding element such that the distal end of the restricting part is housed in the guiding element at the first moment when the supporting arm is expanded.

2. The tissue clamping system according to claim 1, wherein the distal end of the restricting part is housed in the guiding element when an included angle between the two supporting arms is 60° to 150°.

3. The tissue clamping system according to claim 1, wherein the distal end of the restricting part is housed in the guiding element when an included angle between the two supporting arms is 120°.

4. The tissue clamping system according to claim 1, wherein the tissue clamping device further comprises a sealing part, the sealing part surrounding the restricting part.

5. The tissue clamping system according to claim 1, wherein one end of the supporting arm is rotatably connected to the first supporting part, one end of the clamping arm is fixedly connected to the second supporting part, and the other end of the supporting arm is rotatably connected to the other end of the clamping arm.

6. The tissue clamping system according to claim 1, wherein the supporting arm comprises a curved section and a straight section, one end of the curved section is fixedly connected to the straight section and the other end is rotatably connected to the clamping arm; alternatively, one end of the curved section is fixedly connected to the straight section, and one end of the straight section away from the curved section is rotatably connected to the clamping arm.

7. The tissue clamping system according to claim 6, wherein the curved section is curved in a closed position and a degree of curvature of the curved section increases as the clamping arm and the supporting arm move from the closed position to an open position.

8. The tissue clamping system according to claim 1, wherein the clamping arm comprises a connecting section and two supporting sections, two ends of the connecting section are separately connected to the two supporting sections, and an end where the connecting section is located is a free end of the clamping arm; each of the supporting sections comprises a curved segment and an extending segment, one end of the curved segment is connected to the extending segment, and the other end is connected to the connecting section, and an end of the curved segment away from the extending segment is not in the same plane as the extending segment, so that the connecting section is away from an axial central axis of the tissue clamping device.

9. The tissue clamping system according to claim 8, wherein the extending segment comprises a curved rod and a straight rod connected to the curved rod, an end of the curved rod away from the straight rod being connected to the curved segment.

10. The tissue clamping system according to claim 9, wherein there are two clamping arms, and in the closed state, a connection region of the curved rod and the curved section of one clamping arm abuts against a connection region of the curved rod and the curved segment of the other clamping arm.

* * * * *